US009943370B2

(12) United States Patent
Asseln et al.

(10) Patent No.: US 9,943,370 B2
(45) Date of Patent: Apr. 17, 2018

(54) ADVANCED METHODS AND TECHNIQUES FOR DESIGNING KNEE IMPLANT COMPONENTS

(71) Applicant: CONFORMIS, INC., Bedford, MA (US)

(72) Inventors: Malte Asseln, Aachen (DE); Klaus Radermacher, Aachen (DE)

(73) Assignee: ConforMIS, Inc., Billerica, MA (US)

( * ) Notice: Subject to any disclaimer, the term of this patent is extended or adjusted under 35 U.S.C. 154(b) by 736 days.

(21) Appl. No.: 14/169,093

(22) Filed: Jan. 30, 2014

(65) Prior Publication Data

US 2014/0222390 A1 Aug. 7, 2014

Related U.S. Application Data

(60) Provisional application No. 61/758,753, filed on Jan. 30, 2013.

(51) Int. Cl.
| | |
|---|---|
| *G06F 17/50* | (2006.01) |
| *A61B 19/00* | (2006.01) |
| *A61F 2/30* | (2006.01) |
| *A61B 34/10* | (2016.01) |
| *A61F 2/38* | (2006.01) |
| *A61F 2/46* | (2006.01) |

(52) U.S. Cl.
CPC ............. *A61B 19/50* (2013.01); *A61B 34/10* (2016.02); *A61F 2/30942* (2013.01); *A61B 2034/105* (2016.02); *A61F 2/38* (2013.01); *A61F 2/389* (2013.01); *A61F 2002/30948* (2013.01); *A61F 2002/30952* (2013.01); *A61F 2002/4668* (2013.01)

(58) Field of Classification Search
CPC ...... A61B 34/10; A61B 19/50; A61F 2/30942
USPC .................................................. 703/1
See application file for complete search history.

(56) References Cited

U.S. PATENT DOCUMENTS

| | | | |
|---|---|---|---|
| 5,682,886 A | 11/1997 | Delp et al. ............. | 128/653.1 |
| 5,735,277 A | 4/1998 | Schuster ................ | 128/653.1 |
| 5,871,018 A | 2/1999 | Delp et al. ............. | 128/898 |
| 6,161,080 A * | 12/2000 | Aouni-Ateshian . | G06F 19/3437 |
| | | | 600/587 |
| 6,510,334 B1 * | 1/2003 | Schuster ............ | A61F 2/30942 |
| | | | 128/920 |
| 8,234,097 B2 | 7/2012 | Steines et al. ........... | 703/1 |

(Continued)

FOREIGN PATENT DOCUMENTS

| | | | |
|---|---|---|---|
| DE | 44 34 539 | 4/1996 | ............ A61F 2/38 |
| EP | 0 704 193 | 4/1996 | ............ A61F 2/30 |
| EP | 1074229 | 2/2001 | ............ A61F 2/38 |

OTHER PUBLICATIONS

Bidwell et al. ("Total Knee Arthroplasty",The SurgicalTechnologist, 2006, pp. 13-21).*

(Continued)

*Primary Examiner* — Omar Fernandez Rivas
*Assistant Examiner* — Iftekhar Khan
(74) *Attorney, Agent, or Firm* — Sunstein Kann Murphy & Timbers LLP

(57) ABSTRACT

Disclosed are various advanced methods, devices, and systems for implants, tools and techniques that facilitate the surgical repair of a knee joint while allowing retention of more natural kinematics and preserving controlled rotation and translation of the repaired joint.

14 Claims, 3 Drawing Sheets

(56) References Cited

U.S. PATENT DOCUMENTS

| | | | |
|---|---|---|---|
| 8,480,754 B2 | 7/2013 | Bojarski et al. ............ 623/20.35 |
| 8,690,945 B2 | 4/2014 | Fitz et al. .................. 623/16.11 |
| 8,790,410 B2* | 7/2014 | Kazanovicz ....... A61B 17/8095 |
| | | | 623/16.11 |
| 9,020,788 B2 | 4/2015 | Lang et al. ........................ 703/6 |
| 2003/0236473 A1 | 12/2003 | Dore et al. .................... 600/587 |
| 2004/0204760 A1* | 10/2004 | Fitz .................... A61F 2/30756 |
| | | | 623/14.12 |
| 2005/0267584 A1* | 12/2005 | Burdulis, Jr. ....... A61F 2/30942 |
| | | | 623/20.19 |
| 2007/0198022 A1* | 8/2007 | Lang .................... A61B 17/154 |
| | | | 606/88 |
| 2009/0024131 A1* | 1/2009 | Metzger ............. A61B 17/1764 |
| | | | 606/88 |
| 2009/0131941 A1* | 5/2009 | Park ..................... A61B 17/154 |
| | | | 606/87 |
| 2010/0076564 A1* | 3/2010 | Schilling ................ A61B 17/68 |
| | | | 623/20.14 |
| 2011/0029091 A1* | 2/2011 | Bojarski ............. A61F 2/30942 |
| | | | 623/20.32 |
| 2011/0144760 A1* | 6/2011 | Wong .................. A61F 2/30942 |
| | | | 623/20.14 |
| 2011/0214279 A1* | 9/2011 | Park ....................... B23P 17/04 |
| | | | 29/592 |
| 2011/0282473 A1* | 11/2011 | Pavlovskaia ........... A61B 5/055 |
| | | | 700/98 |
| 2011/0295378 A1* | 12/2011 | Bojarski ............. A61F 2/30942 |
| | | | 623/20.35 |
| 2011/0305379 A1* | 12/2011 | Mahfouz ............... A61F 2/3094 |
| | | | 382/131 |
| 2012/0041446 A1* | 2/2012 | Wong .................. A61B 17/1703 |
| | | | 606/96 |
| 2013/0166254 A1* | 6/2013 | Grimm .................. A61B 34/10 |
| | | | 703/1 |
| 2013/0338781 A1* | 12/2013 | Bordeaux ........... A61F 2/30734 |
| | | | 623/20.16 |
| 2015/0073562 A1* | 3/2015 | Landon ................... A61F 2/389 |
| | | | 623/20.34 |

OTHER PUBLICATIONS

Delp et al., A Graphics-Based Software System to Develop and Analyze Models of Musculoskeletal Structures, Comput. Biol. Med., vol. 25, No. 1, pp. 21-34, 1995.
Delp et al., "Computer Assisted Knee Replacement", Clinical Orthopaedics, pp. 49-56, Sep. 1998.
U.S. Appl. No. 12/660,529, filed Feb. 25, 2010, now U.S. Pat. No. 8,480,754.
U.S. Appl. No. 12/712,072, filed Feb. 24, 2010, now U.S. Pat. No. 8,234,097.
U.S. Appl. No. 13/397,457, filed Feb. 15, 2012, now U.S. Pat. No. 9,020,788.
U.S. Appl. No. 12/777,878, filed May 11, 2010, now U.S. Pat. No. 8,690,945.

* cited by examiner

ADVANCED METHODS AND TECHNIQUES FOR DESIGNING KNEE IMPLANT COMPONENTS

RELATED APPLICATIONS

This application claims the benefit of U.S. Provisional Application No. 61/758,753, entitled "Advanced Methods and Techniques for Designing Knee Implant Components" and filed Jan. 30, 2013, the disclosure of which is incorporated herein by reference in its entirety.

TECHNICAL FIELD

The present disclosure relates to improved methods and techniques for designing and/or selecting patient adapted (e.g., patient-specific and/or patient-engineered) orthopedic implants, as well as related methods, designs, systems and models, such as, for example, those described in U.S. patent application Ser. No. 13/397,457, entitled "Patient-Adapted and Improved Orthopedic Implants, Designs And Related Tools," filed Feb. 15, 2012, and published as U.S. Patent Publication No. 2012-0209394, which is incorporated herein by reference in its entirety.

BACKGROUND

When a patient's knee is severely damaged, such as by osteoarthritis, rheumatoid arthritis, or post-traumatic arthritis, it may be desirous to repair and/or replace portions or the entirety of the knee with a total or partial knee replacement implant. Knee replacement surgery, also known as total knee arthroplasty (TKA), can help relieve pain and restore function in injured and/or severely diseased knee joints, and is a well-tolerated and highly successful procedure. Where a total joint replacement is needed, it is often performed by a surgeon via an open procedure, although various less-invasive and/or minimally-invasive approaches have been proposed and developed as well.

In a typical TKA procedure, once the underlying bony anatomical support structures have been prepared, both the tibia and femur can receive an artificial joint component made of metal alloys, high-grade plastics and/or polymers to replace native anatomy and desirably function as a new knee joint. In the case of tibial implant components, the artificial joint can include a metal receiver tray that is firmly fixed to the tibia. In many cases, the tibial implant further includes a medical grade plastic insert (which may also be referred to as a "spacer") that can be attached to the tray and positioned between the femoral component(s) and the tibial tray to create a smooth gliding surface for articulation of the components. Such a system can also allow for inserts of multiple sizes and/or thicknesses, which facilitates in-situ balancing of the knee as well as allowing the placement of inserts of differing designs and/or shapes.

While the implantation of TKA components via surgical procedures is a well accepted procedure that is well tolerated by patients and has a high success rate, standard TKA procedures typically focus on axial and rotational alignment of the prosthesis components and ligament balancing. Even though TKA has been constantly improved, e.g., by introducing navigation techniques, TKA patients often experience poorer functional outcomes than total hip arthroplasty patients, which suggests that additional design factors might warrant consideration.

DETAILED DESCRIPTION

It has been determined that complications can occur when knee kinematics after TKA do not correspond with the physiological conditions. Design considerations, therefore, may be significantly improved when a designer or surgeon takes into account both active and passive motion considerations. One such consideration that may alter or otherwise impact a knee implant design, including the design and/or selection of total as well as partial knee replacement and resurfacing implants, is the understanding that the quadriceps angle (Q-angle) for a knee joint may have a substantial impact on active joint kinematics, and the location, strength and line of action of this anatomical feature should be taken into account in anatomical modeling and TKA implant positioning. Moreover, the Q-angle and related anatomical considerations may significantly impact the design and/or selection of implant components, including the patient-specific, patient-adapted and/or patient-engineered features of such prostheses, particularly the femoral component of the joint implant.

Disclosed are various advanced methods, devices, and systems for implants, tools and techniques that facilitate the surgical repair of a knee joint while allowing retention of more natural kinematics and desirably preserving controlled rotation and translation of the repaired joint. In many embodiments, the procedures described herein can be employed to design, select and/or position implants that provide improved or adequate pain relief, preserve normal axial alignment of the limb, and preserve stability—this, in turn, can potentially reduce wear on the knee components as well as reduce shear stresses at the component-cement-bone interfaces.

The design and/or selection of a given femoral component is an important aspect of knee surgery, and a given femoral component will desirably include patient-specific and/or patient-engineered features. The patient image data and various considerations described herein (as well as data derived from patient-specific data, including patient-engineered data) can be used to specifically design femoral component(s) to create a unique and appropriate patient-specific size and shape for the patient.

In various embodiments, the patient image data may be used to design femoral components that have asymmetric or symmetric medial or lateral sides. The medial or lateral sides may also have different AP or ML dimensions. Also, the condylar groove may also be designed to have a deeper/larger cut, have a variety of shapes, may be obliquely cut, or be a combination of one or more of these shapes and/or designs. In other embodiments, the femoral components may be unicompartmental or bicompartmental, and may be formed in one-piece, two-piece or multi-piece designs.

Q-Angles

Figure 1:
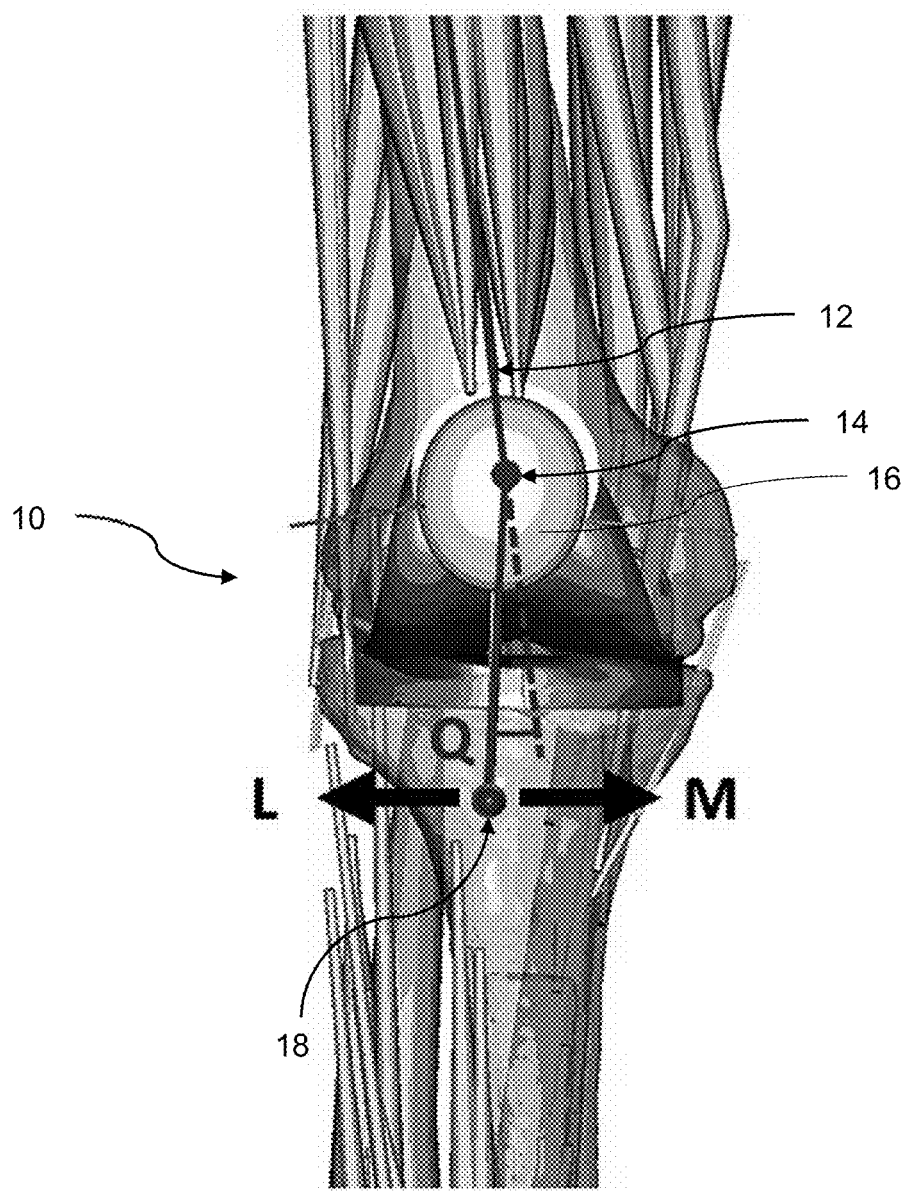
FIG. 1 depicts a knee joint and soft tissue model.

The Q-angle for a knee joint 10, as illustrated in FIG. 1, can be simply defined as the angle between (1) a first line 12 from the anterior superior iliac spine to the center 14 of the patella 16 and (2) a second line from the center 14 of the patella 16 to the tibial tuberosity (TT) 18. In many cases, these anatomical structures or reference points thereof can be readily visualized using pre-operative visualization techniques, including techniques such as conventional methods of x-ray imaging and processing, x-ray tomosynthesis, ultrasound (including A-scan, B-scan and C-scan), computed tomography (CT scan), magnetic resonance imaging (MRI), optical coherence tomography, single photon emission tomography (SPECT) and positron emission tomography (PET), T1 and T2-weighted spin-echo imaging, gradient recalled echo (GRE) imaging, magnetization transfer contrast (MTC) imaging, fast spin-echo (FSE) imaging, contrast enhanced imaging, rapid acquisition relaxation enhancement (RARE) imaging, gradient echo acquisition in the steady state (GRASS), and driven equilibrium Fourier transform (DEFT) imaging, among other imaging techniques and methods well known in the art. In one embodiment, knee imaging studies could be performed in both extension and flexion.

As an initial step, patient anatomical information can obtained from patient measurements and imaging through the various methods described herein. Such information can include various information regarding a targeted femur, tibia and patella of a targeted knee joint, which can include information regarding the patient's femoral/tibial/patellar shape, length, width, condyle dimensions, features and slopes, angles (e.g., trochlear angles, Q angle) trochlea characteristics, tibial characteristics, tibial tuberosity, medial/lateral slopes, tibial spine height, coronal curvatures, sagittal curvatures and general joint dimensions, as well as any number of biomechanical or kinematic parameters as described in the foregoing sections and as known in the art. The information can also include anatomical and biomechanical axes, angle and other information from the patient's opposing joint, as well as information regarding adjacent joint structures (i.e., hip and/or ankle information) from the treated leg or the opposing leg or both. Additional information collected can include body weight, race, gender, activity level, health conditions, other disease or medical conditions, etc.

As one factor in the design and modeling of a patient's anatomical structures, an increased Q angle can potentially be a risk factor for patellar subluxation, and a pathological position of the TT can be related to patellofemoral pain and knee instability. The Q-angle can be influenced by the position of the TT, and consequently patient specific medial/lateral TT position influences not only the patellofemoral but also tibiofemoral biomechanics. If active knee kinematics do not correspond to passive knee kinematics defined by the ligament situation, this aspect should be considered for implant design and positioning.

In one exemplary anatomical model simulation of a patient's anatomy, implemented using a multi-body software AnyBody™ (commercially available from AnyBody™ Technology A/S, Denmark), a knee joint was represented by articulating surfaces of a standard prosthesis and as having 6 degrees of freedom. A force-dependent kinematics method was used for the calculations, and intra-articular passive structures, such as collateral and cruciate ligaments, were implemented. In this exemplary simulation, the muscular apparatus consisted of 159 muscles per leg. The joint coordinate system by Grood et al. (Grood E. S., et al.: J Biomech, 105, 136-144, 1983, which is incorporated herein by reference in its entirety) was used to determine the tibiofemoral kinematics. Accordingly, reference axes were identified based on anatomical landmarks on the femur and tibia, and the Q-angle was measured in a reference position (two leg stance). As input parameter for the sensitivity analysis, the insertion point of the patella tendon was translated medially 9 mm (towards M of FIG. 1) and laterally 15 mm (towards L of FIG. 1) from the initial position in equidistant steps of 3 mm. Changes in tibiofemoral kinematics and Q-angle were recorded and tabulated.

Results of Simulation and Analysis

Figure 2:
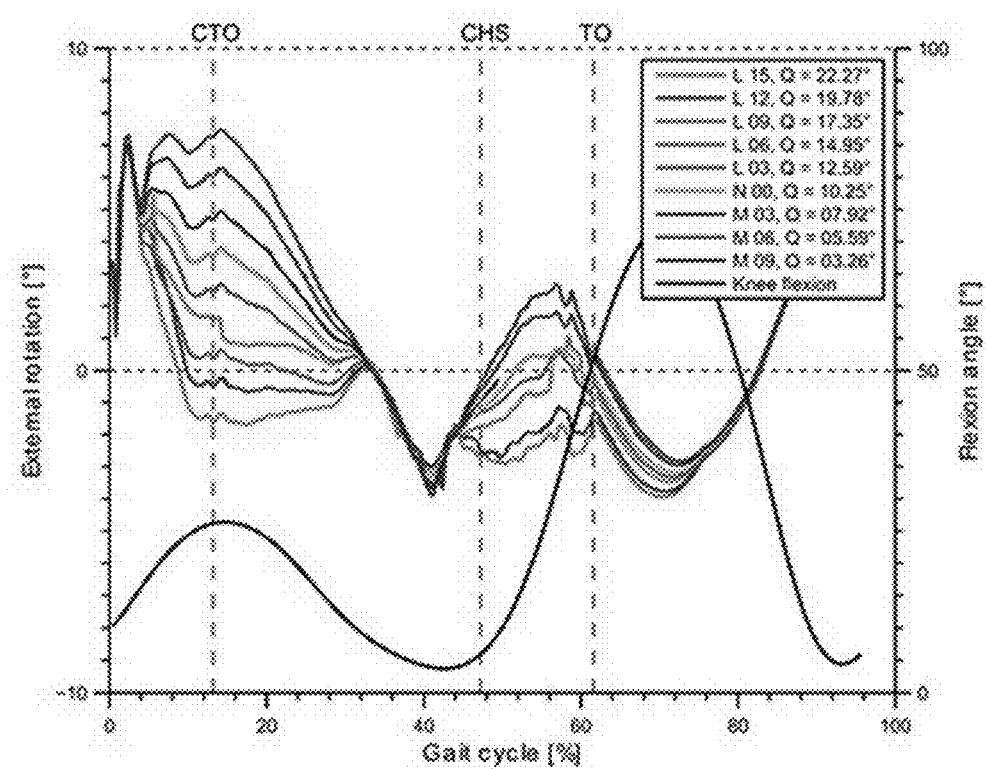
FIG. 2 depicts a graph of the relationship between the position of the tibial tuberosity and internal/external rotation in a knee joint simulation.

The Q-angle was about 10° in the initial position, which lies in the physiological range. It changed approximately 2.5° with a gradual shift of 3 mm, confirming the impact of the individual TT position on active knee kinematics. Depending on the position of the TT, the tibiofemoral kinematics, particularly the internal/external rotation of the tibia, were significantly affected. Lateralization of the TT decreased the external rotation of the tibia with respect to the femur, whereas a medialization caused an increase of the external rotation (see FIG. 2). During contralateral toe off (CTO), the external rotation was +7.5° for a medial transfer of 9 mm and −1.4° for a lateral transfer of 15 mm, respectively.

Figure 3:
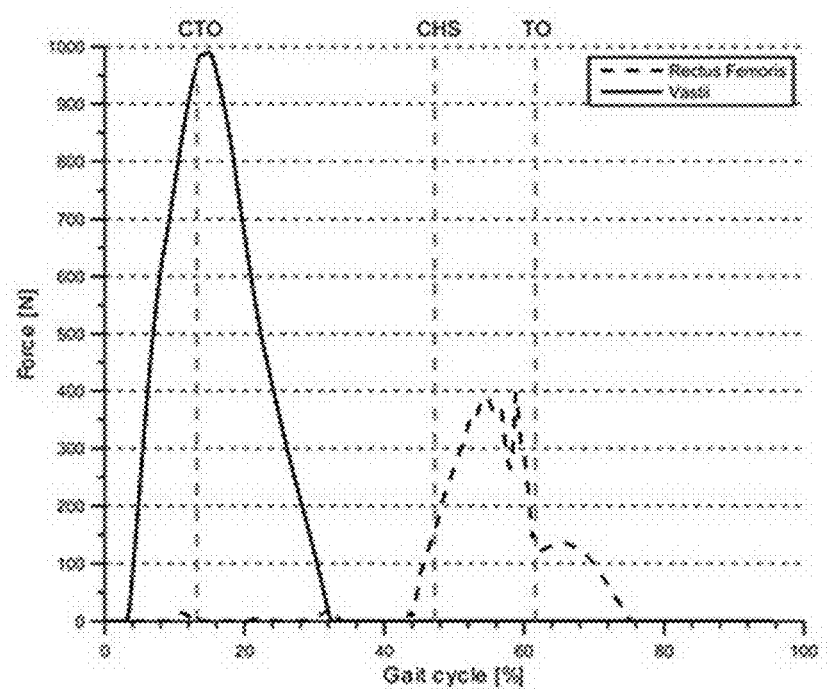
FIG. 3 depicts a graph of the relationship between the activation of the quadriceps and observed kinematic changes.

The differences in external rotation were almost zero at the beginning, in the middle (30-40%) and at the end of the gait cycle. The evaluation of the activation pattern of the quadriceps muscle showed correlation: the higher the activation of the quadriceps, the greater were the observed changes in kinematics (See FIG. 3). It appeared that there were no changes occurred during zero activation, which can be the case for low flexion angles. And thus, the rotation depended on the loading condition, indicating that muscle action significantly changes knee kinematics.

Because knee kinematics can be strongly affected by the Q-angle, which is directly associated with the position of the TT, the activation of the quadriceps muscle can play a significant role and will desirably be accounted for in anatomical feature modeling and implant design and/or selection. As active kinematic modeling can show significant differences as compared to passive kinematic modeling, simply balancing the ligaments intraoperatively may result in a suboptimal ligament situation during active motion subsequent to joint replacement. Since the Q-angle can vary widely between gender and individual patients, this anatomical feature will desirably be considered, e.g., in preoperative model based planning of patient specific TKA. Moreover, the differential effects of different training stages of the quadriceps as well as the relative consequences for pre- and postoperative training and rehabilitation may be valuable inputs in anatomical modeling and design in various instances.

In at least one exemplary embodiment, an anatomical model can be designed and utilized that accounts for the sensitivity of active knee kinematics related to the medial/lateral position of the TT (corresponding to a variation of the Q-angle), potentially by employing a complex multi-body model with a dynamic simulation of an entire gait cycle.

In various alternative embodiments, the anatomical model or the design and/or selection of the implant components (or their positioning) can include simulations of the effects of TT medialization, which may partially correct abnormal contact pressures and adjust patella maltracking. Such medialization may simulate and/or induce a change in the orientation of the patella tendon (either virtually or after the surgical procedure) which can be used in a variety of ways to alter the biomechanics of the knee.

Additionally or alternatively, in some embodiments a patient-specific femoral implant component may be designed with a trochlear groove having a position, shape, and/or orientation such that it is aligned (sagitally, coronally, and/or with respect to a resulting force) with the TT at one or more flexion angles (optionally, throughout the entire range of flexion).

Modeling Considerations

In various embodiments, Q-angle data and relevant anatomical feature information may be relevant to the measuring and deriving desired anatomical features, and may be utilized in the design and/or selection of a desired joint implant. If desired, weighting parameters may be assigned to various measurements or series of measurements (or other collected or derived information), as well as to one or more joint surfaces, including opposing joint surfaces.

Anatomical measurements and considerations, including data relevant to a patient's Q-angle, can be combined with information regarding any misalignment and or the proper mechanical alignment of a patient's limb to preoperatively design and/or select one or more features of a joint implant and/or implant procedure. For example, based on the difference between the patient's misalignment and the proper mechanical axis, a knee implant and implant procedure can be designed and/or selected preoperatively to include implant and/or resection dimensions that substantially realign the patient's limb to correct or improve a patient's alignment deformity. In addition, the process can include selecting and/or designing one or more surgical tools (e.g., guide tools or cutting jigs) to direct the clinician in resectioning the patient's bone in accordance with the preoperatively designed and/or selected resection dimensions.

In certain embodiments, the degree of deformity correction that may be necessary to establish a desired limb alignment can be calculated based on information from the alignment of a virtual model of a patient's limb. The virtual model can be generated from patient-specific data, such 2D and/or 3D imaging data of the patient's limb. The deformity correction can correct varus or valgus alignment or antecurvatum or recurvatum alignment. In various embodiments, the desired deformity correction returns the leg to normal alignment, for example, a zero degree biomechanical axis in the coronal plane and absence of genu antecurvatum and recurvatum in the sagittal plane.

The preoperatively designed and/or selected implant or implant component, resection dimension(s), and/or cutting jig(s) can be employed to correct a patient's alignment deformity in a single plane, for example, in the coronal plane or in the sagittal plane, in multiple planes, for example, in the coronal and sagittal planes, and/or in three dimensions. In one embodiment, where the patient's lower limb is misaligned in the coronal plane, for example, a valgus or varus deformity, the deformity correction can be achieved by designing and/or selecting one or more of a resection dimension, an implant component thickness, and/or an implant component surface curvature that adjusts the mechanical axis or axes into alignment in one or more planes. For example, a lower limb misalignment can be corrected in a knee replacement by designing or selecting one or more of a femoral resection dimension, a femoral implant component thickness, a femoral implant component surface curvature, a tibial resection dimension, a tibial implant component thickness, a tibial implant component insert thickness, and/or a tibial implant component surface curvature to adjust the femoral mechanical axis and tibial mechanical axis into alignment in the coronal plane.

In certain embodiments, bone cuts and implant shape including at least one of a bone-facing or a joint-facing surface of the implant that can be designed or selected to achieve normal joint kinematics.

In certain embodiments, a computer program simulating biomotion of one or more joints, such as, for example, a knee joint, or a knee and ankle joint, or a hip, knee and/or ankle joint can be utilized. In certain embodiments, patient-specific imaging data can be fed into this computer program. For example, a series of two-dimensional images of a patient's knee joint or a three-dimensional representation of a patient's knee joint can be entered into the program. Additionally, two-dimensional images or a three-dimensional representation of the patient's ankle joint and/or hip joint may be added.

Alternatively, patient-specific kinematic data (including the various data previously described), for example obtained in a gait lab, can be fed into the computer program. Alternatively, patient-specific navigation data, for example generated using a surgical navigation system, image guided or non-image guided can be fed into the computer program. This kinematic or navigation data can, for example, be generated by applying optical or RF markers to the limb and by registering the markers and then measuring limb movements, for example, flexion, extension, abduction, adduction, rotation, and other limb movements.

Optionally, other data including anthropometric data may be added for each patient. These data can include but are not limited to the patient's age, gender, weight, height, size, body mass index, and race. Desired limb alignment and/or deformity correction can be added into the model. The position of bone cuts on one or more articular surfaces as well as the intended location of implant bearing surfaces on one or more articular surfaces can be entered into the model.

A patient-specific biomotion model can be derived that includes combinations of parameters listed herein. The biomotion model can simulate various activities of daily life including normal gait, stair climbing, descending stairs, running, kneeling, squatting, sitting and any other physical activity. The biomotion model can start out with standardized activities, typically derived from reference databases. These reference databases can be, for example, generated using biomotion measurements using force plates and motion trackers using radiofrequency or optical markers and video equipment.

The biomotion model can then be individualized with use of patient-specific information including at least one of, but not limited to the patient's age, gender, weight, height, body mass index, and race, the desired limb alignment or deformity correction, and the patient's imaging data, for example, a series of two-dimensional images or a three-dimensional representation of the joint for which surgery is contemplated.

An implant shape including associated bone cuts generated in the preceding optimizations, for example, limb alignment, deformity correction, bone preservation on one or more articular surfaces, can be introduced into the model. Many exemplary parameters can be measured in a patient-specific biomotion model, such as, for example, those identified in Table 1 below.

TABLE 1

Exemplary parameters measured in a patient-specific biomotion model for various implants

| Joint implant | Measured Parameter |
|---|---|
| knee | Medial femoral rollback during flexion |
| knee | Lateral femoral rollback during flexion |
| knee | Patellar position, medial, lateral, superior, inferior for different flexion and extension angles |
| knee | Internal and external rotation of one or more femoral condyles |
| knee | Internal and external rotation of the tibia |
| knee | Flexion and extension angles of one or more articular surfaces |
| knee | Anterior slide and posterior slide of at least one of the medial and lateral femoral condyles during flexion or extension |
| knee | Medial and lateral laxity throughout the range of motion |
| knee | Contact pressure or forces on at least one or more articular surfaces, e.g. a femoral condyle and a tibial plateau, a trochlea and a patella |
| knee | Contact area on at least one or more articular surfaces, e.g. a femoral condyle and a tibial plateau, a trochlea and a patella |
| knee | Forces between the bone-facing surface of the implant, an optional cement interface and the adjacent bone or bone marrow, measured at least one or multiple bone cut or bone-facing surface of the implant on at least one or multiple articular surfaces or implant components. |
| knee | Ligament location, e.g. ACL, PCL, MCL, LCL, retinacula, joint capsule, estimated or derived, for example using an imaging test. |
| knee | Ligament tension, strain, shear force, estimated failure forces, loads for example for different angles of flexion, extension, rotation, abduction, adduction, with the different positions or movements optionally simulated in a virtual environment. |
| knee | Potential implant impingement on other articular structures, e.g. in high flexion, high extension, internal or external rotation, abduction or adduction or any combinations thereof or other angles/positions/movements. |
| knee | Relevant Q-Angle and associated anatomical feature measurements |
| Hip, shoulder or other joint | Internal and external rotation of one or more articular surfaces |
| Hip, shoulder or other joint | Flexion and extension angles of one or more articular surfaces |
| Hip, shoulder or other joint | Anterior slide and posterior slide of at least one or more articular surfaces during flexion or extension, abduction or adduction, elevation, internal or external rotation |
| Hip, shoulder or other joint | Joint laxity throughout the range of motion |
| Hip, shoulder or other joint | Contact pressure or forces on at least one or more articular surfaces, e.g. an acetabulum and a femoral head, a glenoid and a humeral head |
| Hip, shoulder or other joint | Forces between the bone-facing surface of the implant, an optional cement interface and the adjacent bone or bone marrow, measured at least one or multiple bone cut or bone-facing surface of the implant on at least one or multiple articular surfaces or implant components. |
| Hip, shoulder or other joint | Ligament location, e.g. transverse ligament, glenohumeral ligaments, retinacula, joint capsule, estimated or derived, for example using an imaging test. |
| Hip, shoulder or other joint | Ligament tension, strain, shear force, estimated failure forces, loads for example for different angles of flexion, extension, rotation, abduction, adduction, with the different positions or movements optionally simulated in a virtual environment. |
| Hip, shoulder or other joint | Potential implant impingement on other articular structures, e.g. in high flexion, high extension, internal or external rotation, abduction or adduction or elevation or any combinations thereof or other angles/positions/movements. |

The above list is not meant to be exhaustive, but only exemplary. Any other biomechanical parameter known in the art can be included in the analysis.

The resultant biomotion data can be used to further optimize the implant design with the objective to establish normal or near normal kinematics. The implant optimizations can include one or multiple implant components. Implant optimizations based on patient-specific data including image based biomotion data can include, but are not limited to:

Changes to external, joint-facing implant shape in coronal plane

Changes to external, joint-facing implant shape in sagittal plane

Changes to external, joint-facing implant shape in axial plane

Changes to external, joint-facing implant shape in multiple planes or three dimensions Changes to internal, bone-facing implant shape in coronal plane Changes to internal, bone-facing implant shape in sagittal plane Changes to internal, bone-facing implant shape in axial plane Changes to internal, bone-facing implant shape in multiple planes or three dimensions Changes to perimeter of implant shape in coronal plane Changes to perimeter of implant shape in sagittal plane Changes to perimeter of implant shape in axial plane Changes to perimeter of implant shape in multiple planes or three dimensions Changes to implant notch shape in coronal plane Changes to implant notch shape in sagittal plane Changes to implant notch shape in axial plane Changes to implant notch shape in multiple planes or three dimensions Changes to one or more bone cuts, for example with regard to depth of cut, orientation of cut Various embodiments contemplate any single one or combinations of the above or all of the above on at least one articular surface or implant component or multiple articular surfaces or implant components.

When changes are made on multiple articular surfaces or implant components, these can be made in reference to or linked to each other. For example, in the knee, a change made to a femoral bone cut based on patient-specific biomotion data can be referenced to or linked with a concomitant change to a bone cut on an opposing tibial surface, for example, if less femoral bone is resected, the computer program may elect to resect more tibial bone.

Similarly, if a femoral implant shape is changed, for example on an external surface, this can be accompanied by a change in the tibial component shape. This is, for example, particularly applicable when at least portions of the tibial bearing surface negatively-match the femoral joint-facing surface.

Similarly, if the footprint of a femoral implant is broadened, this can be accompanied by a widening of the bearing surface of a tibial component. Similarly, if a tibial implant shape is changed, for example on an external surface, this can be accompanied by a change in the femoral component shape. This is, for example, particularly applicable when at least portions of the femoral bearing surface negatively-match the tibial joint-facing surface.

Similarly, if a patellar component radius is widened, this can be accompanied by a widening of an opposing trochlear bearing surface radius, or vice-versa.

If desired, computerized modeling of the implant, the anatomy and/or combinations thereof can be utilized to virtually determine a resection cut strategy for the patient's femur and/or tibia that provides minimal bone loss optionally while also meeting other user-defined parameters such as, for example, maintaining a minimum implant thickness, using certain resection cuts to help correct the patient's misalignment, removing diseased or undesired portions of the patient's bone or anatomy, and/or other parameters. This general step can include one or more of the steps of (i) simulating resection cuts on one or both articular sides (e.g., on the femur and/or tibia), (ii) applying optimized cuts across one or both articular sides, (iii) allowing for non-co-planar and/or non-parallel femoral resection cuts (e.g., on medial and lateral corresponding portions of the femur) and, optionally, non-co-planar and/or non-parallel tibial resection cuts (e.g., on medial and lateral corresponding portions of the tibia), and (iv) maintaining and/or determining minimal material thickness. The minimal material thickness for the implant selection and/or design can be an established threshold, for example, as previously determined by a finite element analysis ("FEA") of the implant's standard characteristics and features (or analysis of individual portions of the implant). Alternatively, the minimal material thickness can be determined for the specific implant, for example, as determined by an FEA of the implant's standard and patient-specific characteristics and features. If desired, FEA and/or other load-bearing/modeling analysis may be used to further optimize or otherwise modify the individual implant design, such as where the implant is under or over-engineered than required to accommodate the patient's biomechanical needs, or is otherwise undesirable in one or more aspects relative to such analysis. In such a case, the implant design may be further modified and/or redesigned to more accurately accommodate the patient's needs, which may have the side effect of increasing/reducing implant characteristics (i.e., size, shape or thickness in global and/or localized areas of the implant) or otherwise modifying one or more of the various design "constraints" or limitations currently accommodated by the present design features of the implant. If desired, this step can also assist in identifying for a surgeon the bone resection design to perform in the surgical theater and it also identifies the design of the bone-facing surface(s) of the implant components, which may substantially negatively-match the patient's resected bone surfaces, at least in part.

By optimizing implant shape in this manner, it is possible to establish normal or near normal kinematics. Moreover, it is possible to avoid implant related complications, including but not limited to implant complications such as anterior notching, notch impingement, posterior femoral component impingement in high flexion, and other complications associated with existing implant designs. Similar implant complications can be avoided for tibial components as well. For example, certain designs of the femoral components of traditional knee implants have attempted to address limitations associated with traditional knee implants in high flexion by altering the thickness of the distal and/or posterior condyles of the femoral implant component or by altering the height of the posterior condyles of the femoral implant component. Since such traditional implants follow a one-size-fits-all approach, they are typically limited to altering only one or two aspects of an implant design. However, with the design approaches described herein, various features of an implant component can be designed for an individual to address multiple issues, including issues associated with high flexion motion. For example, designs as described herein can alter an implant component's bone-facing surface (for example, number, angle, and orientation of bone cuts), joint-facing surface (for example, surface contour and curvatures) and other features (for example, implant height, width, and other features) to address issues with high flexion together with other issues.

Biomotion models for a particular patient can be supplemented with patient-specific finite element modeling or other biomechanical models known in the art. Resultant forces in the knee joint can be calculated for each component for each specific patient. The implant can be engineered to the patient's load and force demands. For instance, a 125 lb. patient may not need a tibial plateau as thick as a patient with 280 lbs. Similarly, the polyethylene can be adjusted in shape, thickness and material properties for each patient. For example, a 3 mm polyethylene insert can be used in a light patient with low force and a heavier or more active patient may need an 8 mm polymer insert or similar device.

In various embodiments, the design and/or placement of a tibial component can be influenced (or otherwise "driven") by various factors of the femoral geometry. For example, it may be desirous to rotate the design of some or all of a tibial component (i.e., the entirety of the component and its support structure or some portion thereof, including the tibial tray and/or the articulating poly insert and/or merely the surface orientation of the articulating surface of the tibial insert) to some degree to accommodate various features of the femoral geometry, such as the femoral epicondylar axis, posterior condylar axis, medial or lateral sagittal femoral J-curves, or other femoral axis or landmark. In a similar manner, the design and/or placement of the femoral component (i.e., the entirety of the femoral component and its support structure or some portion thereof, including the orientation and/or placement of one or more condyles, condyle surfaces and/or the trochlear groove) can be influenced (or "driven") by various factors of the tibial geometry, including various tibial axes, shapes, medial and/or lateral slopes and/or landmarks, e.g., tibial tuberosity, Q-angle, etc. Both femoral and tibial components can be influenced in shape or orientation by the shape, dimensions, biomechanics or kinematics of the patellofemoral joint, including, for example, trochlear angle and Q-angle, sagittal trochlear geometry, coronal trochlear geometry, etc.

Utilizing Database Models

If desired, various of the collected and/or derived patient-specific information (as well as any models or optional weighting parameters) can be compared to identify one or more "matching subjects" from one or more reference databases, comparing features from the matching subject to the patient-specific information, and optionally creating a comparison or "weighting score" to evaluate and display the results of the various comparisons (relative to individual feature comparisons and/or an overall composite score for the comparison of each subject). The databases can comprise information from various sources, including cadaveric data, imaging, biomechanical or kinematic data, historic data and/or data regarding previous knee implant cases from various manufacturers, including ConforMIS-specific case data. Such data can be specific to gender, age, weight, health, size, etc., or can be selected based on weighting (as previously described) or other criteria.

Depending upon the chosen design and/or selection procedure, various methods may manually or automatically select one or more anatomic shapes or features from one or more matching subjects to create one or more "derived anatomic matches" and/or to modify the patient-specific data. The "derived anatomic matches" may comprise the features from one or more subjects, or may comprise a composite anatomy derived from such shapes and/or subjects (which may also be identified and/or derived utilizing a weighting score, if desired). In addition, or in place of, this step, the method may utilize the matching subject data to normalize or "smooth" the patient-specific data, which can desirably correct or normalize the patient-specific data and potentially correct the patient-specific data for inherent deformities like osteophytes, axis deformity and/or cartilage degradation.

The derived anatomic matches and/or modified patient-specific data (either alone or in combination with the original patient-specific data) can be utilized to derive, design and/or select an appropriate implant design and placement to treat the joint in a desired manner.

Surgical Jigs, Guides and Resection Tools

A variety of guides, jigs and/or resection tools may be designed and/or selected to assist surgeons in preparing a joint for an implant, for example, for resectioning one or more of a patient's biological structures during a joint implant procedure. In certain embodiments, a guide tool includes at least one feature for directing a surgical instrument to deliver a patient-engineered, patient-specific or standard feature(s) to the patient's biological structure, for example, a resected hole or a resection cut for engaging a patient-engineered implant peg or a patient-engineered implant bone-facing surface. In addition to any patient-engineered features, in certain embodiments one or more of the guide tool's bone-facing surfaces can be designed to be patient-specific so that they substantially negatively-match a portion of the patient's joint surface. In addition or alternatively, one or more of the guide tool's bone-facing surfaces can be standard in shape.

The guides, jigs and/or resection tools further can include at least one aperture for directing movement of a surgical instrument, for example, a securing pin or a cutting tool. One or more of the apertures can be designed to guide the surgical instrument to deliver a patient-optimized placement for, for example, one or more securing pins or resection cuts. In addition or alternatively, one or more of the apertures can be designed to guide the surgical instrument to deliver a standard placement for, for example, for one or more securing pins or resection cuts. Alternatively, certain guide tools can be used for purposes other than guiding a drill or cutting tool. For example, balancing and trial guide tools can be used to assess knee alignment and/or fit of one or more implant components or inserts. Also, the balancing and trial guide tools can be used in combination with other jigs to deliver a more accurate or precise resected surface of the bone.

The guide tools described herein can include any combination of patient-specific features, patient-engineered features, and/or standard features. For example, a patient-specific guide tool can include at least one feature that is preoperatively designed and/or selected to substantially match one or more of the patient's biological features. A standard guide tool can include at least one feature that is selected from among a family of limited options, for example, selected from among a family of 5, 6, 7, 8, 9, or 10 options. Moreover, in certain embodiments a set or kit of guide tools is provided in which certain guide tools in the set or kit include patient-specific, patient-engineered and/or standard features.

The various implant components described herein can be machined, molded, casted, manufactured through additive techniques such as laser sintering or electron beam melting or otherwise constructed out of a metal or metal alloy such as cobalt chromium. Similarly, various insert components may be machined, molded, manufactured through rapid prototyping or additive techniques or otherwise constructed out of a plastic polymer such as ultra high molecular weight polyethylene. Other known materials, such as ceramics including ceramic coating, may be used as well, for one or both components, or in combination with the metal, metal alloy and polymer described above. It should be appreciated by those of skill in the art that an implant may be constructed as one piece out of any of the above, or other, materials, or in multiple pieces out of a combination of materials. For example, a tray component constructed of a polymer with a two-piece insert component constructed one piece out of a metal alloy and the other piece constructed out of ceramic.

Each of the components may be constructed as a "standard" or "blank" in various sizes or may be specifically formed for each patient based on their imaging data and anatomy. Computer modeling may be used and a library of virtual standards may be created for each of the components. A library of physical standards may also be amassed for each of the components. Imaging data including shape, geometry, e.g., M-L, A-P, and S-I dimensions, then can be used to select the standard component, e.g., a femoral component or a tibial component or a humeral component and/or a glenoid component that most closely approximates the select features of the patient's anatomy. Typically, these components will be selected so that they are slightly larger than the patient's articular structure that will be replaced in at least one or more dimensions. The standard component is then adapted to the patient's unique anatomy, for example by removing overhanging material, e.g., using machining.

The step of designing an implant component and/or guide tool as described herein can include both configuring one or more features, measurements, and/or dimensions of the implant and/or guide tool (e.g., derived from patient-specific data from a particular patient and adapted for the particular patient) and manufacturing the implant. In certain embodiments, manufacturing can include making the implant component and/or guide tool from starting materials, for example, metals and/or polymers or other materials in solid (e.g., powders or blocks) or liquid form. In addition or alternatively, in certain embodiments, manufacturing can include altering (e.g., machining) an existing implant component and/or guide tool, for example, a standard blank implant component and/or guide tool or an existing implant component and/or guide tool (e.g., selected from a library). The manufacturing techniques to making or altering an implant component and/or guide tool can include any techniques known in the art today and in the future. Such techniques include, but are not limited to additive as well as subtractive methods, i.e., methods that add material, for example to a standard blank, and methods that remove material, for example from a standard blank.

Any material known in the art can be used for any of the implant systems and component described in the foregoing embodiments, for example including, but not limited to metal, metal alloys, combinations of metals, plastic, polyethylene, cross-linked polyethylene's or polymers or plastics, pyrolytic carbon, nanotubes and carbons, as well as biologic materials.

Any fixation techniques and combinations thereof known in the art can be used for any of the implant systems and component described in the foregoing embodiments, for example including, but not limited to cementing techniques, porous coating of at least portions of an implant component, press fit techniques of at least a portion of an implant, ingrowth techniques, etc.

Aspects of embodiments described herein may be successfully applied to other damaged or diseased articulating joints, including procedures where a surgeon desires to preserve natural ligaments and/or other underlying anatomical structures. Such joints can include various other joints of a body, e.g., ankle, foot, elbow, hand, wrist, shoulder, hip, and/or spine. Also, various embodiments described herein can be successfully applied to total knee, bicompartmental or unicompartmental knee surgery.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

What is claimed is:

1. A method of designing an implant for use in treatment of a knee joint of a patient, the method comprising:
receiving patient-specific anatomical information;
generating a model of at least a portion of a femur and a tibia of the knee joint based, at least in part, on the patient-specific information, the at least a portion of the femur including a trochlear groove located at an anatomic position and orientation and having an anatomic shape, and the at least a portion of the tibia including a tibial tuberosity located at an anatomic position;
designing a shape of a joint-facing surface of an implant component based, at least in part, on a shape of a corresponding joint surface in the model;
generating a modified model of the at least a portion of the tibia in which the location of the tibial tuberosity of the tibia is modified so as to be translated medially or laterally relative to the anatomic position of the tibial tuberosity; and
modifying a shape of at least a portion of the joint-facing surface of the implant component based, at least in part, on the translation of the tibial tuberosity.

2. The method of claim 1, wherein the implant component comprises a femoral component.

3. The method of claim 2, wherein the tibial tuberosity is translated medially relative to the anatomic position, and the shape of the at least a portion of the joint-facing surface of the femoral implant component is modified to accommodate increased external rotation of the femur relative to the tibia during flexion of the knee joint.

4. The method of claim 2, wherein the tibial tuberosity is translated laterally relative to the anatomic position, and the shape of the at least a portion of the joint-facing surface of the femoral implant component is modified to accommodate decreased external rotation of the femur relative to the tibia during flexion of the knee joint.

5. The method of claim 1, wherein the implant component comprises a tibial component.

6. The method of claim 5, wherein the tibial tuberosity is translated medially relative to the anatomic position, and the shape of the at least a portion of the joint-facing surface of the tibial implant component is modified to accommodate increased external rotation of the femur relative to the tibia during flexion of the knee joint.

7. The method of claim 5, wherein the tibial tuberosity is translated laterally relative to the anatomic position, and the shape of the at least a portion of the joint-facing surface of the tibial implant component is modified to accommodate decreased external rotation of the femur relative to the tibia during flexion of the knee joint.

8. The method of claim 5, further comprising: designing a shape of a joint-facing surface a femoral implant component based, at least in part, on a shape of a corresponding joint surface in the model; and modifying a shape of at least a portion of the joint-facing surface of the femoral implant component based, at least in part, on the translation of the tibial tuberosity.

9. The method of claim 8, wherein the tibial tuberosity is translated medially relative to the anatomic position, and the shape of the at least a portion of the joint-facing surface of the femoral implant component and the shape of the at least a portion of the joint-facing surface of the tibial implant component are each modified to accommodate increased external rotation of the femur relative to the tibia during flexion of the knee joint.

10. The method of claim 8, wherein the tibial tuberosity is translated laterally relative to the anatomic position, and the shape of the at least a portion of the joint-facing surface of the femoral implant component and the shape of the at least a portion of the joint-facing surface of the tibial implant component are each modified to accommodate decreased external rotation of the femur relative to the tibia during flexion of the knee joint.

11. The method of claim 2, further comprising designing a shape of a trochlear groove of the femoral component based, at least in part, on the anatomic shape of the trochlear groove; and modifying the shape of at least a portion of the trochlear groove of the femoral implant component based, at least in part, on the translation of the tibial tuberosity.

12. The method of claim 2, further comprising designing an orientation of a trochlear groove of the femoral component based, at least in part, on the anatomic orientation of the trochlear groove; and modifying the orientation of at least a portion of the trochlear groove of the femoral implant component based, at least in part, on the translation of the tibial tuberosity.

13. The method of claim 2, further comprising designing a position of a trochlear groove of the femoral component based, at least in part, on the anatomic position of the trochlear groove; and modifying the position of at least a portion of the trochlear groove of the femoral implant component based, at least in part, on the translation of the tibial tuberosity.

14. The method of claim 1, further comprising receiving instructions from a surgeon specifying the translation of the tibial tuberosity.

* * * * *